United States Patent [19]

Weissman

[11] Patent Number: 4,767,332

[45] Date of Patent: Aug. 30, 1988

[54] THREADED DENTAL ANCHOR

[75] Inventor: Bernard Weissman, New York, N.Y.

[73] Assignee: IPCO Corporation, White Plains, N.Y.

[21] Appl. No.: 517,006

[22] Filed: Jul. 25, 1983

Related U.S. Application Data

[63] Continuation-in-part of Ser. No. 361,522, Mar. 23, 1982, abandoned, and a continuation-in-part of Ser. No. 326,851, Dec. 3, 1981.

[51] Int. Cl.[4] ............................................. A61C 5/04
[52] U.S. Cl. ................................................. 433/225
[58] Field of Search ...................... 433/225, 220, 174; 44/387, 420, 421

[56] References Cited

U.S. PATENT DOCUMENTS

| | | | |
|---|---|---|---|
| 4,103,422 | 8/1978 | Weiss et al. | 433/174 |
| 4,171,569 | 10/1979 | Rouins | 433/225 |
| 4,365,958 | 12/1982 | Vlock | 433/225 |

FOREIGN PATENT DOCUMENTS 2255916  5/1974  Fed. Rep. of Germany ...... 433/174

Primary Examiner—Robert Peshock
Attorney, Agent, or Firm—Goodman & Teitelbaum

[57] ABSTRACT

A self-threading dental anchor including a proximal head end providing a manipulating end section for permitting the coupling thereof to a cooperating driving tool, and a threaded anchoring portion extending from the proximal head end. The anchoring portion threads are in the range of 60-100 threads per inch, preferably 84 threads per inch with standard threads and 96 threads per inch with a buttress type thread, to provide for fast insertion with minimum torque. The anchoring portion has an elongated distal pilot end portion in the axial direction approximately equal to the thread pitch of approximately 0.010 to 0.012 inches. A second threaded anchoring portion may be connected to the distal pilot end portion of the first mentioned anchoring portion to provide a frangible reduced thickness portion therebetween, which is readily visible. Preferably, each thread has a height of approximately 0.0020 to 0.0025 inches. Modified embodiments of the dental anchor are provided with stop members spaced preferably midway along the length of each anchoring portion to limit the depth of insertion thereof into a channel which extends into a tooth understructure. The stop members can be formed by providing an unthreaded portion, by deforming, heading, offsetting, stamping, splaying, and the like.

14 Claims, No Drawings

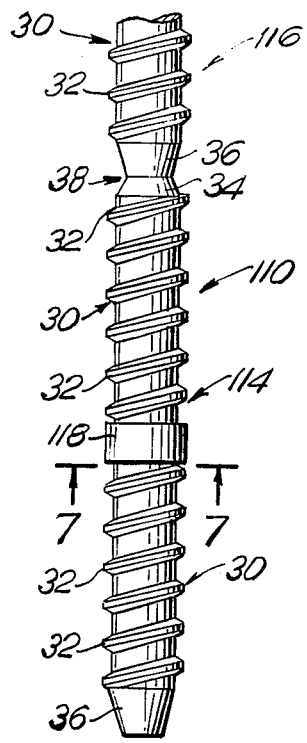
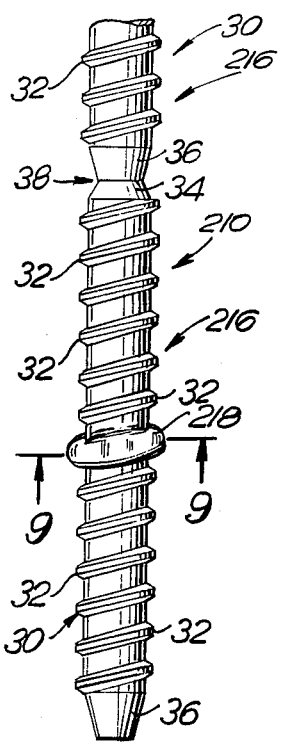
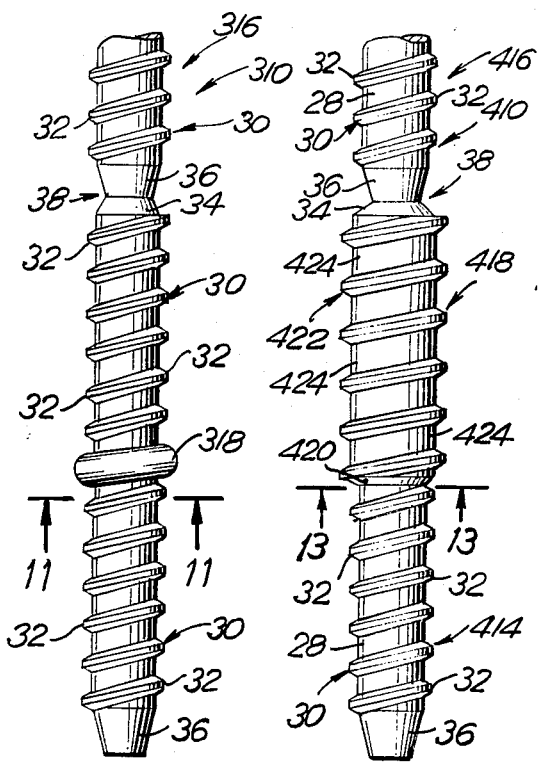
FIG.6  FIG.8  FIG.10  FIG.12
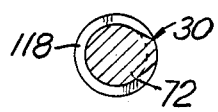
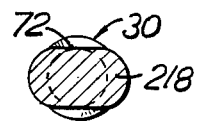
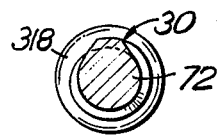
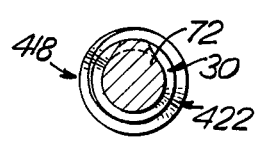
FIG.7  FIG.9  FIG.11  FIG.13
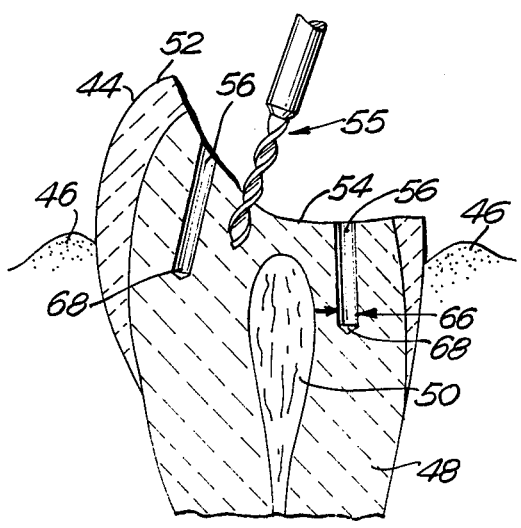
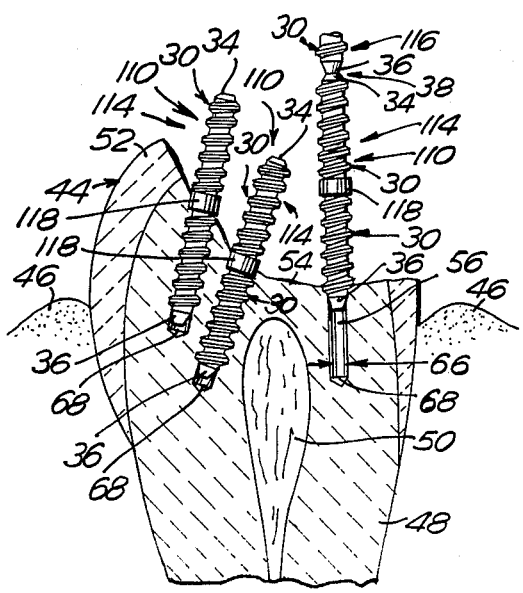
FIG.14  FIG.15

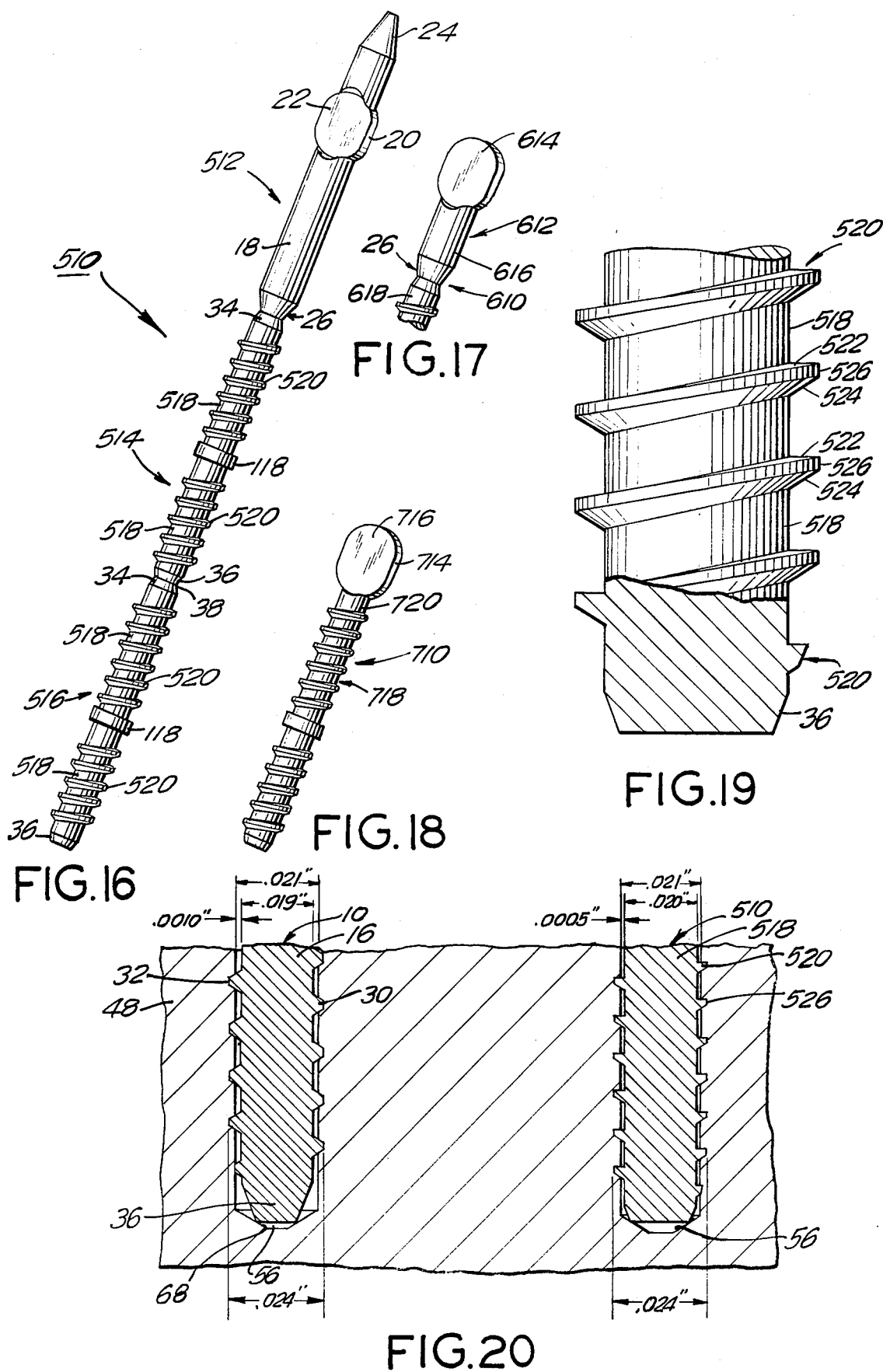

THREADED DENTAL ANCHOR

RELATIONSHIP TO OTHER APPLICATIONS

This is a continuation-in-part application of copending application Ser. No. 361,522, filed Mar. 23, 1982, for a "Threaded Dental Anchor", now abandoned, and a continuation-in-part application of co-pending application Ser. No. 326,851, filed Dec. 3, 1981, for a "Dental Anchor".

BACKGROUND OF THE INVENTION

This invention relates generally to dentistry, and more particularly to dental anchors or pins used for retaining or reinforcing dental restorations.

When the crowns of teeth are severely decayed or fractured, difficulty is encountered in conventional preparations for providing effective retention for the restoration. Techniques are available for utilizing small retentive and/or reinforcing anchors or pins for facilitating such retention. Generally, the decayed or fractured portion of the tooth is removed so as to provide an excavated surface. Then, one or more blind channels are formed into the remaining tooth portion, extending into the dentin from the exposed excavated surface. Reinforcing or anchoring pins are then inserted into the channels. Numerous types of anchors are available including self-threading anchors, pins which are inserted and then retained by cementation, or force fitting anchors retained by an interference fit. Such anchors are inserted so that a free end portion protrudes above the excavated surface. A superstructure is then built upon the exposed excavated surface which is retained by means of the exposed free end portion of the anchors. This method of building up the superstructure on dentition is described in numerous patents and technical articles, by way of example in my U.S. Pat. No. 3,434,209.

The particular pins or dental anchors which are utilized to interconnect the superstructure and anchor it onto the understructure, have been of various types. In my U.S. Pat. No. 3,675,328, there is described a dental anchor having a plurality of threaded sections with each section being capable of being severed apart from the other. In my U.S. Pat. No. 3,675,329, there is provided an anchoring pin with a head, wherein the head extends above the understructure so as to be embedded in the superstructure and provide resistance to displacement. A further dental anchor is provided in my U.S. Pat. No. 4,053,982, which utilizes an L-shaped manipulating portion which can be received in a dental tool for manipulating the anchor into the understructure and also for assisting in the retention of the superstructure. Various types of manipulating portions can also be provided on the dental anchor, as shown in my U.S. Pat. No. 4,202,101, which also describes a hand held driver for use in inserting in the dental structure.

U.S. Pat. No. 3,861,043 describes a dental pin used in building a superstructure on a tooth, the pin including a shaft having a flute at the lower end thereof, with the remainder of the shaft being threaded.

U.S. Pat. No. 4,171,569 describes a dental pin having spaced apart threads formed on a pair of opposing coaxial shafts separated at their center by an enlarged portion serving as a rotating handle. The patent provides for a recommended major diameter of the pins and height of the threads; however it does not provide for any suggestions concerning the number of threads per inch or the pitch of the threads. U.S. Pat. No. 4,334,865 describes a dental pin having a threaded rod with a saw toothed type of thread and an enlarged collar portion serving as a bearing member for the screw.

U.S. Pat. No. 4,365,958 describes a combined dental drill and anchor pin having a stop member disposal therebetween, whereby the drill forms its own hole in the tooth dentin so that the anchor pin is secured in a single insertion step. However, this patent, as the above mentioned patents, does not provide any information with respect to the number of threads per inch or the pitch of the threads.

In the application of anchors of this type, it is of course essential that the practitioner avoid the generation of possible stress upon the dentition during the process of installation. Unless such precautions are observed, crazing or cracking of the understructure may result. The reduction or complete elimination of such possibility has been found to be extremely desirable. In order to eliminate this possibility, it has been found desirable to provide a means to reduce the possibility of excessive insertion stresses, wherein the anchor bottoming against the blind end of the channel and generating possible undesirable stress is eliminated.

Because of the importance of such superstructures in restoring the teeth, numerous technical studies and research programs have been carried out to determine the best type and technique of pin retention. In carrying out such studies, it was necessary to evaluate anchors by insertion into materials which can substitute for the dentin. Such models do not necessarily duplicate the various physical characteristics of the dentin, although typically, high modulus plastic material is utilized as test substitutes for the dentin.

Utilizing these techniques, investigators have studied various parameters effecting the retention and insertion techniques. Parameters which have been studied in detail include anchoring pin type, pin diameter, pin depth, number of pins, the effect of cavity varnish and various dental cements, and the retention in dental amalgam and the like.

For example, it has been found that self-threading anchors have the greatest retention of various types tested. It was also found that retention increases as the diameter of the pin is increased. Greater depth of insertion also increases the retention; however, self-threading anchors have been found to be most retentive for the same depth when compared to friction lock anchors or cemented pins.

Tests have also been carried out in connection with the number of anchors to be utilized, the angle of insertion, and the technique involved in inserting the anchors.

Despite all of the various tests and procedures which have heretofore been carried out, the use of dental anchors has still not been as effective and successful as is theoretically possible. One of the most obvious reasons for the lack of success is that the testing models do not accurately reproduce the dentin characteristic. In addition to having a wide range of moduli values and different compressive and tensile strengths, the dentin has a unique histological structure which includes directional properties. Furthermore, the characteristics of dentin vary, consequently the anchoring technique, for its insertion, must have such characteristics as to be consistently useful and preclude the possibility of injury to surrounding dentition. Accordingly, the various tests which use dentin substitutes to produce their results, while providing conclusions which may be effective for certain dentin properties, do not adequately address all the unique dentin properties and accordingly are not as effective as theoretically predicted.

The most important aspect of using the dental anchors is to ensure the proper amount of retention and at the same time reduce the amount of dentin compression and eliminate adverse effects upon the surrounding dentin. When prior art anchors, and especially the self-threading type of anchors, have been improperly inserted into the blind channels formed in the tooth structure, undesirable stresses have occurred on the existing dentin, especially at the blind end or bottom seat portion when fully inserted.

SUMMARY OF THE INVENTION

One aspect of the threaded anchors which has not been heretofore generally studied concerns the threads on the pin. In most studies utilizing threaded anchors, standard threads are used for a given pin diameter. Heretofore, it has not been realized that the number of threads per inch can greatly influence the anchor pin retention and the extent of dentin stress and damage.

It has now been found that when inserting a threaded anchor pin in dentin material, a lesser number of threads per inch will provide superior results as compared with a threaded anchor pin having a larger number of threads per inch. Utilizing such reduced number of threads per inch, there results a superior anchor pin retention while reducing undesirable dentin stress. Additionally, less torque is needed to insert the anchor, and the insertion speed is increased, in that the number of rotations required to insert the anchor to the desired depth is reduced, as is the magnitude of stress caused during the insertion process itself.

Furthermore, a more efficient process can be used in manufacturing the threaded dental anchors having the reduced number of threads per inch thereon, the minor diameter of the threaded dental anchor can be increased relative to the prior art dental anchors, thereby strengthening the dental anchor of the present invention.

In an embodiment of the invention, in order to further reduce the amount of stress in the seat of the channel in the tooth, the pilot or distal end of the dental anchor has been elongated to space the threads from the seat of the channel, wherein the taper angle of the pilot or distal end with respect to the circumference of the dental anchor of the present invention has been decreased relative to the taper angle of the prior art dental pins.

In another embodiment of the invention, in order to further reduce the amount of stress in the surrounding dental structure, a buttress type of thread is utilized which permits a slight increase in the number of threads per inch to provide a reduced pitch, and also permits an increase in the minor diameter of the pin to increase the retention capabilities of the pin while reducing the dental stresses.

The dental anchor of the present invention has additionally been modified in order to further reduce the amount of the stress in the seat of the channel in the tooth, each of the modified dental anchors can include a stop member disposed along its length to limit the depth of insertion of the dental anchor into the channel which extends into the dentin from the excavated surface of the tooth. These stop members can be formed on the dental anchor in many ways, such as for example by providing an unthreaded portion, by deforming, heading, offsetting, stamping, splaying, and the like.

Accordingly, it is an object of the present invention to provide a dental anchor pin which avoids the aforementioned problems of the prior art anchor pins.

A further object of the present invention is to provide a dental anchor pin of the threaded type which provides superior results compared with self-threading dental pins of the prior art.

A further object of the present invention is to provide a self-threading dental anchor pin which contains less threads per inch than the prior art comparable dental pins.

Yet a further object of the present invention is to provide a dental anchor pin which provides a dental anchor pin which provides improved holding power and reduces the amount of dentin damage during insertion.

Still another object of the present invention is to provide a dental anchor pin having a unique thread which provides improvements over prior art dental pins.

Another object of the present invention is to provide a dental anchor pin having a minor diameter which is greater than the minor diameter of the prior art comparable dental pins.

And another object of the present invention is to provide a dental anchor pin having an elongated pilot or distal end relative to the pilot or distal ends of the prior art comparable dental pins.

Yet another object of the present invention is to provide a dental anchor pin, which includes a depth-limiting portion so as to avoid bottoming out of the dental anchor pin in the channel formed in the understructure, thereby avoiding the possibility of stresses or cracks forming in the understructure, particularly at the seat portion of the channel.

A further object of the present invention is to provide a dental anchor pin as described above, wherein the depth-limiting portion includes a stop member formed on the dental anchor pin by providing an unthreaded portion, by deforming, heading, offsetting, stamping, splaying, and the like.

Yet a further object of the present invention is to provide a dental anchor pin having a buttress type thread with a unique pitch range and a minor diameter which is greater than the minor diameter of the prior art comparable dental pins.

Briefly, the present invention is directed to a self-threading dental anchor pin having a head or proximal end provided with means for permitting the coupling thereof to a cooperating driving tool. A shank portion extends from the head or proximal end, and has a plurality of threads thereon defined by axially spaced apart crests, the shank portion having less threads per inch and a larger minor diameter than a standard prior art compatible dental anchor pin. The pilot or distal end of the shank portion can be elongated to space the threads from the distal end thereof. In one embodiment of the invention, a buttress type thread is utilized.

A modified form of the present invention includes providing the dental anchor pin with stop means to provide a depth-limiting portion which limits the depth of insertion of the anchor pin into the channel formed in the understructure of the tooth, and prevents contact between the distal end and the seat of the channel, the stop means being disposed along the axial length of the anchor pin, and being spaced from the pilot or distal end thereof. One embodiment includes an unthreaded body portion, another embodiment includes a coined or stamped enlarged body portion, a further embodiment includes an enlarged body portion formed by heading, and yet another embodiment includes an enlarged axially extending body portion.

BRIEF DESCRIPTION OF THE DRAWINGS

With the above and additional objects and advantages in view, as will hereinafter appear, this invention comprises the devices, combinations and arrangements of parts hereinafter described by way of example, and illustrated in the accompanying drawings of preferred embodiments in which:

FIG. 6 is a fragmented perspective view illustrating a modified threaded dental anchor in accordance with the present invention;

FIG. 7 is a sectional view taken along line 7—7 of FIG. 6;

FIG. 8 is a fragmented perspective view illustrating another modified threaded dental anchor in accordance with the present invention;

FIG. 9 is a sectional view taken along line 9—9 of FIG. 8;

FIG. 10 is a fragmented perspective view illustrating a further modified threaded dental anchor in accordance with the present invention;

FIG. 11 is a sectional view taken along line 11—11 of FIG. 10;

FIG. 12 is a fragmented perspective view illustrating yet another modified threaded dental anchor in accordance with the present invention;

FIG. 13 is a sectional view taken along line 13—13 of FIG. 12;

FIG. 14 is an elevational view, partly in cross-section, showing the channels being formed in the tooth of FIGS. 3 and 4;

FIG. 15 is an elevational view, partly in cross-section, illustrating the modified dental anchors of FIG. 6 being inserted into the tooth of FIG. 14;

FIG. 16 is a perspective view illustrating a threaded dental anchor in accordance with another embodiment of the present invention;

FIG. 17 is a fragmented perspective view showing the upper end portion of a modified form of threaded dental anchor in accordance with the present invention;

FIG. 18 is a perspective view showing the modified upper portion of yet another threaded dental anchor in accordance with the present invention;

FIG. 19 is a fragmented elevational view, partially in section, showing the distal end portion of the threaded dental anchors of FIGS. 16 and 18; and FIG. 20 is an enlarged elevational view in cross section, comparing the dental anchor of FIG. 1 with the dental anchor of either FIGS. 16 or 18 when the same are inserted in the tooth or dentition.

In the various figures of the drawings, like characters designate like parts.

DETAILED DESCRIPTION OF THE PREFERRED EMBODIMENTS

Figures 1, 2:
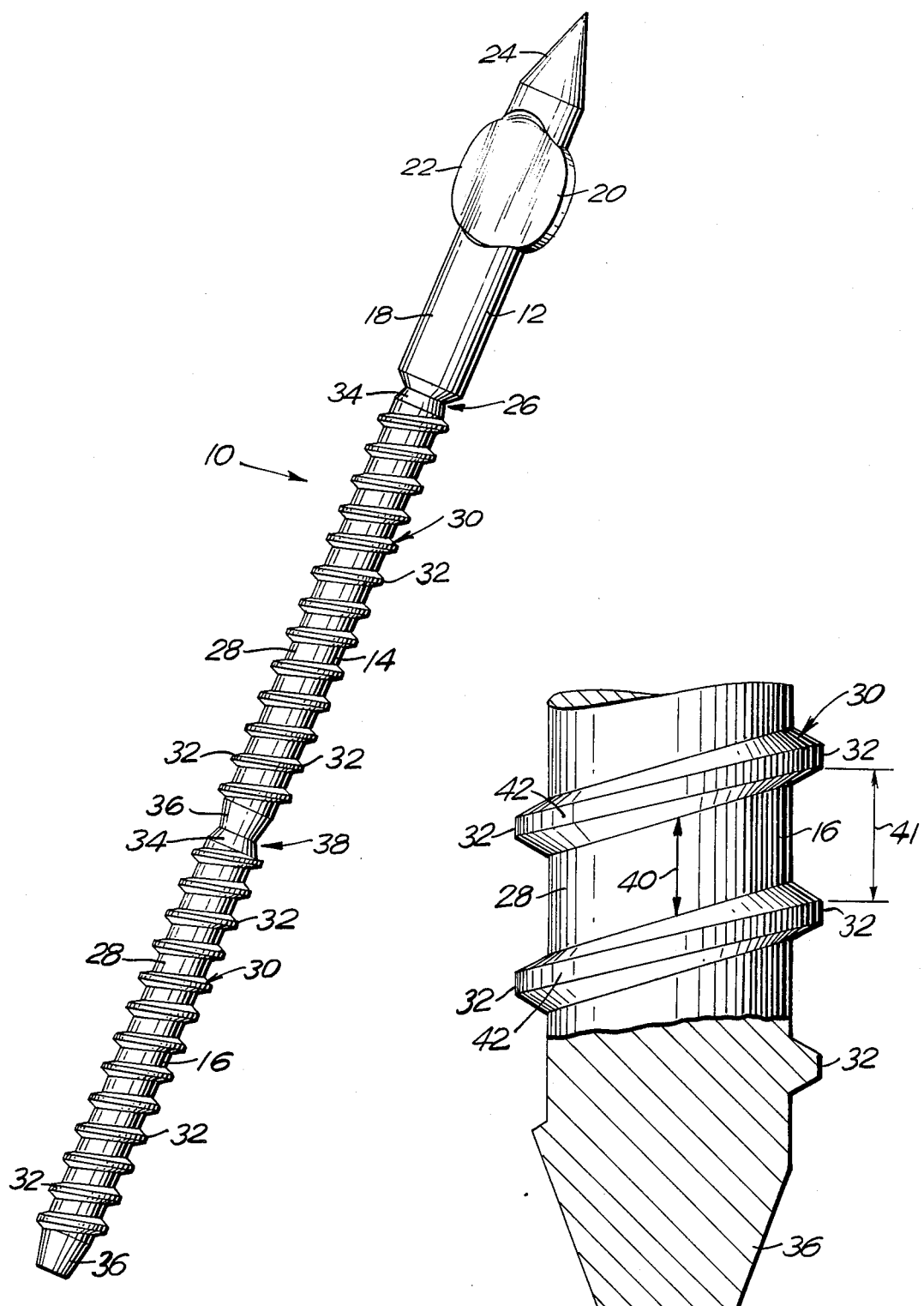
FIG. 1 is a perspective view illustrating the threaded dental anchor in accordance with one embodiment of the present invention.
FIG. 2 is a fragmented elevational view, partly in section, showing the distal end portion of the threaded dental anchor of FIG. 1.

The drawings will now be discussed in detail, wherein FIG. 1 illustrates a dental anchor 10 according to the present invention. The dental anchor 10 includes a head or proximal end to define a manipulating end section 12, an intermediate or second threaded anchoring section 14, and a lower or first threaded anchoring section 16.

The manipulating end section 12 includes a cylindrical body portion 18 having a pair of wing portions 20, 22 stamped or coined therein to provide a torque transfer mechanism, the wing portions 20, 22 extending transversely outwardly from the cylindrical body portion 18 to provide flat surfaces on each side thereof and arcuately extending edges. The upper end of the manipulating section 12 is provided with a conical end 24, which functions as a proximal pilot for inserting the manipulating section into a dental tool or sleeve. The manipulating end section 12 is coupled to the second anchoring section 14 by means of a frangible, reduced thickness portion 26, so that the manipulating section 12 can be severed from the second anchoring section 14 after the second anchoring section 14 has been inserted into a channel in the understructure of a tooth.

It is noted, that the manipulating end section 12, is similar to the manipulating end section shown in my U.S. Pat. No. 4,202,101, and is merely shown by way of example. Accordingly, numerous other types of manipulating end sections could be used, as are well-known in the art, and as are described in my aforementioned patents. Therefore, any prior art manipulating end section could be used, which is structured to be received in a chuck of a conventional dental handpiece, or in a conventional hand driver or wrench. As disclosed in my U.S. Pat. No. 4,202,101, to which reference may be made, the manipulating end section 12 as shown herein in FIG. 1, is adapted to be received in a shank or sleeve, preferably of a plastic material, which is adapted to be received in either the dental handpiece or hand driver.

The first and second anchoring sections 16, 14 are similar, and therefore only one of these anchoring sections requires a full description. It is noted, that a dental anchor having two anchoring sections joined together is disclosed in my U.S. Pat. No. 3,675,328, to which reference may be made, so that only the differences in the present invention will be set forth below.

The anchoring sections 14, 16 each have a body portion 28 provided with a helical thread 30 having crests 32. The anchoring sections 14, 16 have a major diameter of approximately 0.024 inches and a minor diameter of approximately 0.019 inches, to provide a threaded height of approximately 0.0025 inches. The threads per inch is in the range of 60–100, wherein 84 threads per inch are preferred, which provides a pitch of approximately 0.012 inches. Therefore, each anchoring section 14, 16 having a length of approximately 0.177 inches, would have approximately 14 threads thereon.

Each anchoring section 14, 16 has an upper chamfered end 34 and an opposite tapered pilot or distal end 36. The chamfered end 34 has a 45 degree bevel thereon, whereby the chamfered end 34 of the second anchoring section 14 is connected to the manipulating end section 12 to define the reduced thickness portion 26, and the chamfered end 34 of the first anchoring section 16 is connected to the pilot or distal end 36 of the second anchoring section 14 to define a second frangible, reduced thickness portion 38 therebetween. It is noted, that the second reduced thickness portion 38 has a smaller diameter or dimension than the first mentioned reduced thickness portion 26 to insure the severance of the second reduced thickness portion 38 before the severance of the reduced thickness portion 26, as set forth in my U.S. Pat. No. 3,675,328.

As shown more clearly in FIG. 2, the pilot or distal end 36 tapers downwardly from the body portion 28 at approximately 20 degrees to provide an elongated structure. The length of the pilot or distal end relative to the axis of the anchoring section is approximately 0.012 inches, which is approximately equal to the pitch of the thread 30. Furthermore, the width of the minor diameter between the roots of adjacent threads of the thread 30 at 40 is approximately 0.0095 inches, and the distance 41 between the crests 32 of the adjacent threads is approximately 0.0105 inches, whereby each of the threads of the thread 30 has a flat 42 at the crest thereof of approximately 0.0015 inches. Accordingly, from the above description and the showing in FIG. 2, the distance 40 between the roots of the thread 30 at the minor diameter is at least twice the root thickness of the thread 30 at the minor diameter, whereby the ratio of the distance 40 (0.0095 inches) to the thread pitch (0.012 inches) is approximately 4:5.

It is noted, that though the dental anchor 10 as shown in FIG. 1 has two anchoring sections 14, 16, the present invention would also be applicable to dental anchors having only one threaded anchoring section. Furthermore, the present invention would also be applicable to dental anchors having the manipulating end section fixedly connected to the threaded anchoring section, as shown in my U.S. Pat. No. 3,434,209.

Figure 3:
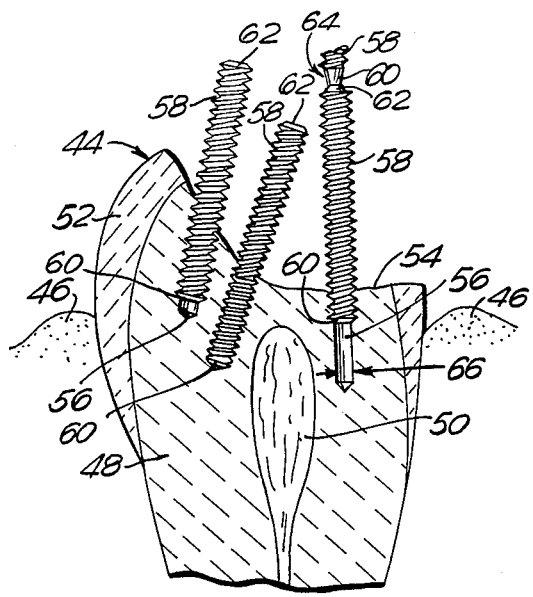
FIG. 3 is an elevational view, partly in cross-section, showing a tooth or dentition with its surface excavated prior to building a superstructure thereon, illustrating the prior art dental anchors being inserted therein.

FIG. 3 illustrates the prior art, similar to the disclosure in my prior U.S. Patents showing a tooth or dentition 44 in the soft tissue or gingiva 46 of the human gum. As is well-known to those skilled in the art, the body 48 of the tooth 44 is formed of dentin and encloses a pulp channel 50. The dentin projecting from the gingiva 46 is covered by a layer of enamel 52. In order to prepare the dentition 44 for building a superstructure thereon, a portion of the enamel 52 and a portion of the dentin is excavated to remove the decay and the undermined tooth structure so as to provide an excavated surface 54 with the decay removed.

The first step in providing the superstructure, is to provide a plurality of channels 56, preferably non-parallel, extending into the dentin or body 48 from the uncovered, excavated surface 54 as shown in FIG. 14. For this purpose, a conventional spiral drill 55 is urged into the dentin in a conventional manner, whereby the bit of the drill preferably has a major diameter of approximately 0.021 inches, and a tip having a taper angle of approximately 118 degrees to form a corresponding channel. After the required number of channels have been made, a prior art threaded dental anchor 58 is inserted into each of the channels 56. The pilot or distal end of each anchor 58 is provided with a transverse, bevelled end surface 60, which has an approximately 30 degree taper with the body portion of the dental anchor. The other end of the dental anchor 50 is provided with a transverse bevelled end surface 62, which has an approximately 45 degree taper. The chamfered end surfaces 60, 62 when joined together as one dental anchor define a frangible, reduced thickness portion 64 to insure the severance of the two threaded anchors when the first anchor is seated in the tooth. It is apparent, that the dimension 66, representing the major diameter of the drilled channel 56, is less than the major diameter of the threaded dental anchor 58, so that the dental anchor can be self-threaded into the channel 56. The prior art dental anchors are provided with approximately 127 threads per inch.

It has been noted, as shown in FIG. 3, that the prior art dental anchors 58, are not always fully inserted into the channels 56, wherein there is no consistency in the insertion thereof. Due to excessive resistance which may develop while the dental anchor 58 is being self-threaded into the channel, the reduced thickness portion 64 may shear too early so that the dental anchor 58 is not fully seated, whereby the bevelled end surface 60, which is approximately 0.003 inches, is spaced from the bottom of the channel 56. Therefore, though full insertion of the dental anchor 58 up to the bottom of the channel is desired, it is not always obtained.

Figure 4:
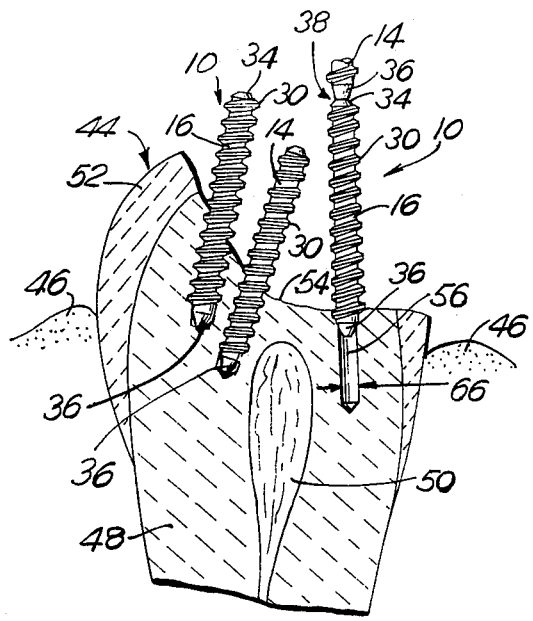
FIG. 4 is an elevational view, partly in cross-section, similar to FIG. 3, illustrating the dental anchors of the present invention being inserted into the tooth or dentition.

FIG. 4 is similar to FIG. 3, showing two dental anchors 10 of the present invention fully inserted into the channels 56 provided in the tooth 44, and a third dental anchor 10 being inserted into a third channel 56. Because of the structure of the dental anchor 10 of the present invention, including the thread 30 and the pilot or distal end 36, the self-threading thereof is faster and the stresses are reduced during the insertion thereof, and the insertion is consistent to provide the desired degree of insertion of the dental anchor 10 into the channel 56 in the tooth 44. Furthermore, the reduced thickness portion 38 between the first and second anchoring sections 16, 14 is more visible than the prior art, so that the point of shearing thereof is more readily determinable.

Figure 5:
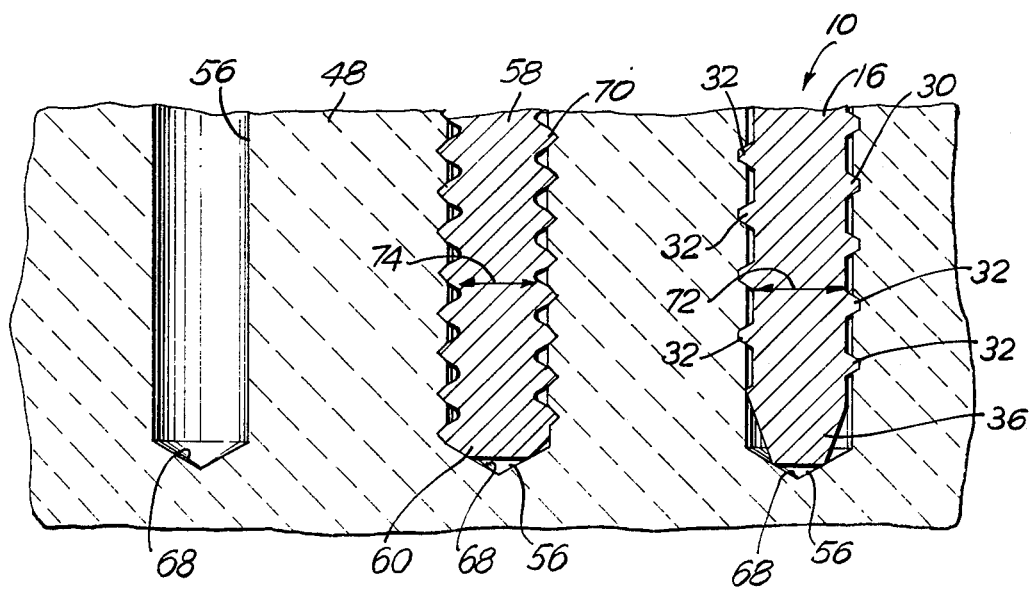
FIG. 5 is an enlarged elevational view in cross-section, comparing the prior art dental anchor with the dental anchor of the embodiment of FIG. 1 of the present invention when same are inserted in the tooth or dentition.
Figures 1, 2:
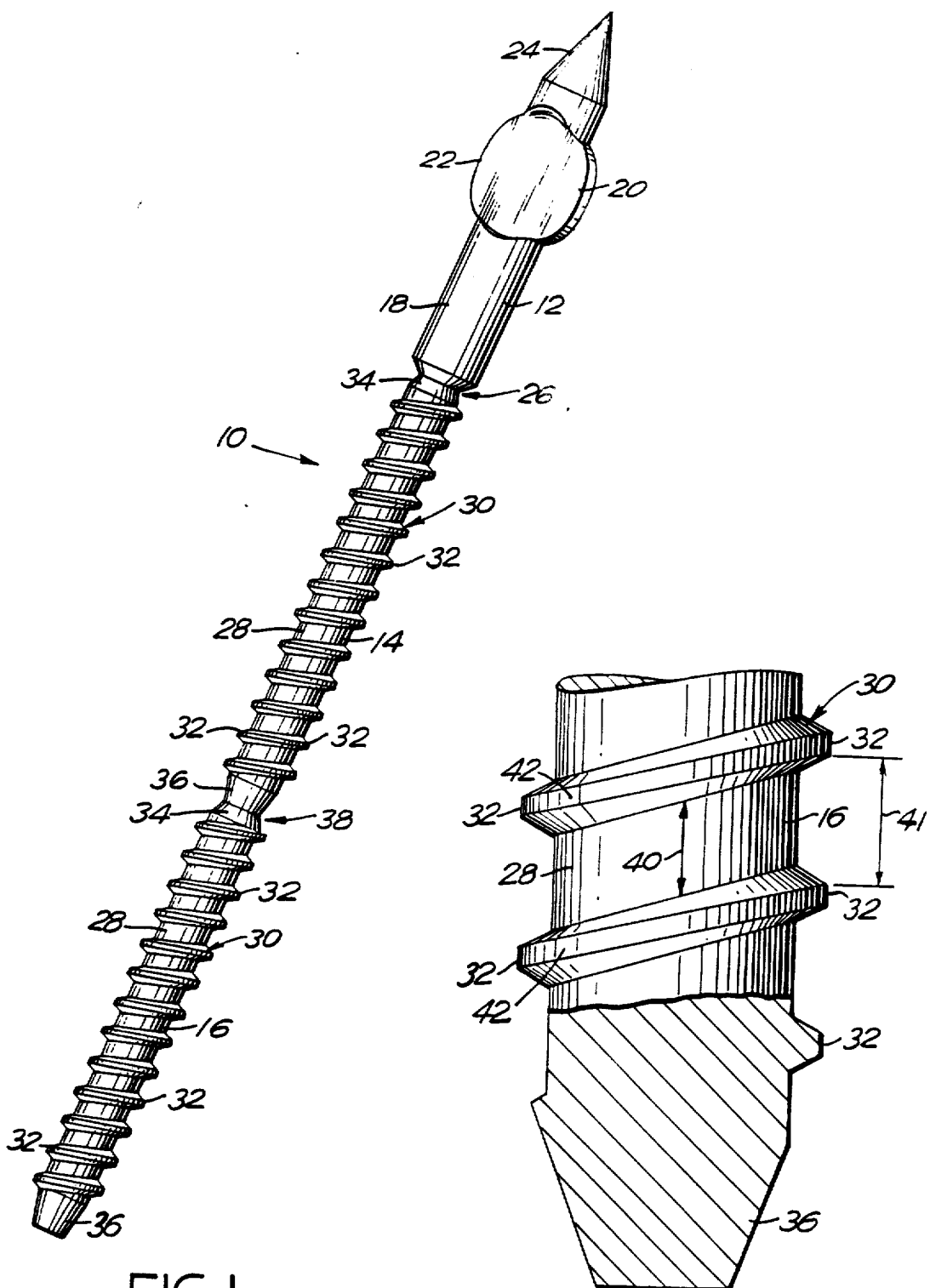
Figure 3:
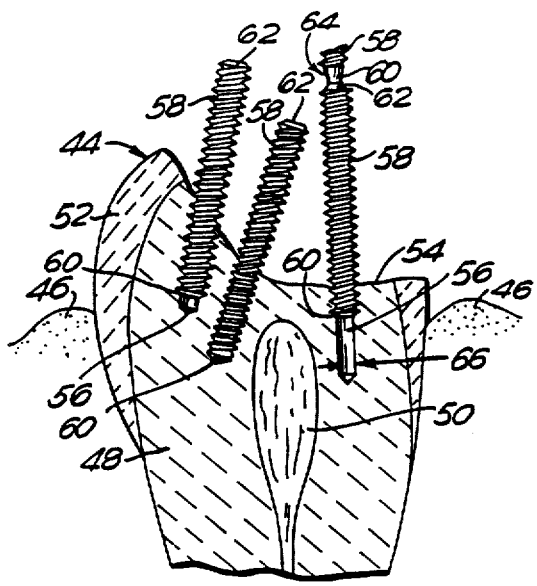
Figure 4:
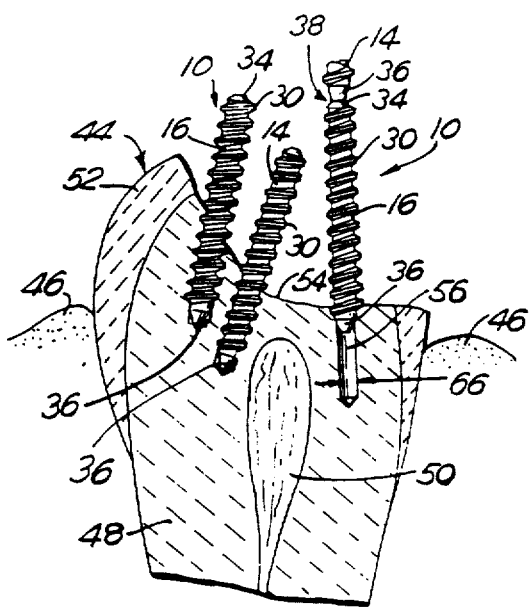
Figure 5:
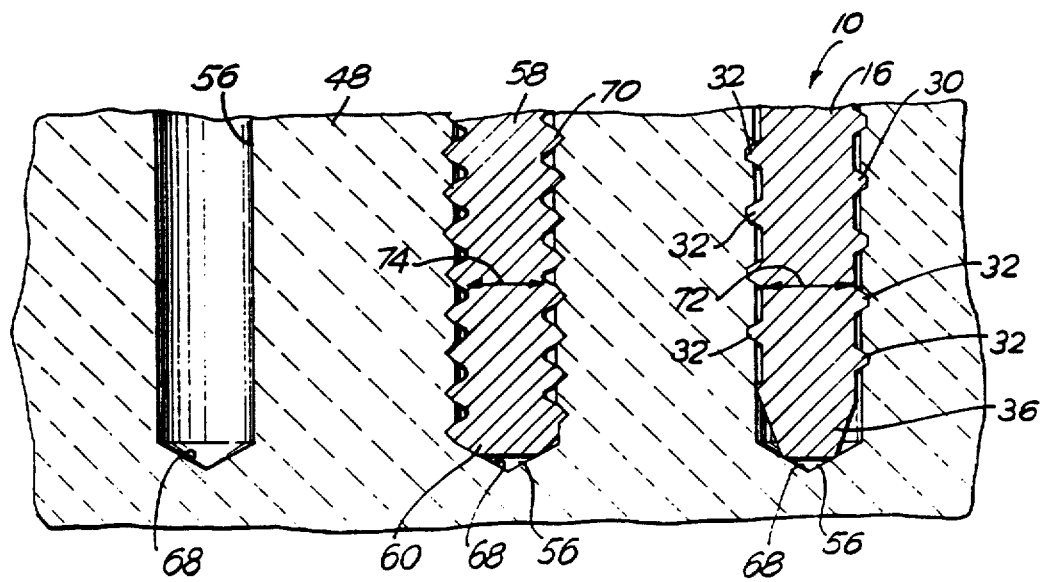

FIG. 5 shows an enlarged section of the body 48 of the tooth having the channels 56 drilled therein, each channel having a seat portion 68. As clearly shown, the thread 70 of the prior art dental anchor 58 is closer to the seat 68 of the channel than the thread 30 of the dental anchor 10 of the present invention, the thread 30 being spaced by the elongation of the pilot end 36 of the dental anchor 10. Furthermore, the thread 70 of the prior art dental anchor 58 tends to crush more of the dentin of the tooth than the thread 30 of the dental anchor 10. Additionally, as clearly shown, there is more dentin between adjacent threads of the thread 30 than between adjacent threads of the thread 70 of the prior art dental anchor. This increased dentin between the adjacent threads of the thread 30 reduces the stresses and provides for more retention when the dental anchor is being cut or bent prior to building the superstructure on the tooth, the dentin between the adjacent threads being in at least a 2:1 relationship with respect to each thread of the thread 30 due to the 4:5 ratio of the minor diameter width between thread roots to the thread pitch. It is further noted that the minor diameter 72 of the threaded section of the dental anchor 10 of the present invention is larger than the minor diameter 74 of the prior art dental anchor 58, thereby providing more strength to the dental anchor 10 of the present invention.

Referring now to FIGS. 6-13, there are shown modifications of the above-described dental anchor 10, according to the present invention. Each of these modified dental anchor includes a stop member, preferably disposed approximately midway along its length, to limit the depth of insertion of the dental anchor into the channel which extends into the dentin or body 48 from the exposed excavated surface 54 of the tooth 44. These stop members can be formed on the dental anchor in many ways, such as, for example, by providing an unthreaded portion, by deforming, heading, offsetting, stamping, splaying, and the like as described hereinafter below. It is further noted, that once the stop member engages the perimeter of the mouth of the channel, the engagement thereof resists further rotation and will activate the self-shearing mechanism of the dental anchor so that the reduced thickness portion of the dental anchor will shear, and thus the insertion operation of the dental anchor will stop.

FIG. 6 illustrates a modified dental anchor 110, which is similar to the dental anchor 10, having similar anchoring sections 114, 116, each provided with a helical thread 30 having crests 32 and having an upper chamfered end 34 and an opposite tapered pilot or distal end 36, whereby the connected ends 34, 36 define a frangible, reduced thickness portion 38 therebetween. Accordingly, the structure mentioned up to this point is the same as that mentioned above with respect to the dental anchor 10. Furthermore, it is not thought necessary to illustrate the proximal end or manipulating end section, which also would be the same as described above.

Approximately midway along the length of each anchoring section 114, 116, there is provided an unthreaded body portion 118. The unthreaded body portion has an axial length of approximately two to three threads of the thread 30. As shown in FIG. 7, the unthreaded body portion 118 has a diameter of approximately 0.024 inches which is larger than the minor diameter 72 of the remaining threaded section 114, 116, thus the unthreaded body portion 118 defines a stop member for limiting the depth of insertion of the anchoring sections 114, 116 into the channel, formed in the tooth, as will be described hereinafter below.

FIG. 8 illustrates a further modified dental anchor 210, which is again similar to the dental anchor 10, having similar anchor sections 214, 216, each provided with a helical thread 30 having crests 32, and having an upper chamfered end 34, and an opposite tapered pilot or distal end 36, whereby the connected ends 34, 36 define a frangible, reduced thickness portion 38 therebetween. Accordingly, here again, the structure mentioned up to this point is the same as that mentioned above with respect to the dental anchor 10. Furthermore, it is again not thought necessary to illustrate the proximal end or the manipulating end section, which also would be the same as described above.

Approximately midway along the length of each anchoring section 214, 216, the anchoring sections are coined or stamped to provide a flattened, enlarged body portion 218. The body portion 218 extends transversely outwardly in opposite directions from each section to provide flat surfaces on each side thereof and arcuately extending edges, as shown in FIG. 9. Thus, because the body portion 218 has a larger transverse dimension than the minor diameter 72 or the thread 30 of the remaining threaded section 214, 216, the body portion 218 defines a stop member for limiting the depth of insertion of the anchoring sections 214, 216 into the channel formed in the tooth, as will be described below by way of example.

FIG. 10 illustrates another modified dental anchor 310, which is again similar to the dental anchor 10, having a similar anchoring sections 314, 316, each provided with a helical thread 30 having crests 32, and having an upper chamfered end 34 and an opposite tapered pilot or distal end 36, whereby the connected ends 34, 36 define a frangible reduced thickness portion 38 therebetween. Accordingly, the structure mentioned up to this point is the same as that mentioned above with respect to the dental anchor 10. Furthermore, again it is not thought necessary to illustrate the proximal end or manipulating end section, which again would be the same as described above.

Again, approximately midway along the length of each anchor section 314, 316, there is provided an enlarged circular body portion 318, the enlarged body portion 318 being formed when the anchoring sections 314, 316 are headed in a conventional manner. As shown in FIG. 11, the enlarged body portion 318 has a larger diameter than the minor diameter 17 and the thread 30 of the remaining threaded section 314, 316, thus the enlarged body portion 318 defines a stop member for limiting the depth of insertion of the anchoring sections 314, 316 into the channel formed in the tooth, as will be described below by way of example.

FIG. 12 illustrates yet another modified dental anchor 410, which is substantially similar to the dental anchor 10, having similar lower anchoring section portions 414, 416, each provided with a helical thread 30 having crests 32, and having an upper chamfered end 34 and an opposite tapered pilot or dental end 36, whereby the connected ends 34, 36 again define a frangible reduced thickness portion 38 therebetween. Accordingly, the structure mentioned up to this point is the same as that mentioned above with respect to the dental anchor 10. Furthermore, again it is not thought necessary to illustrate the proximal end or manipulating end section, which would again be the same as described above.

Extending from approximately the midway point of its length to the upper end of each anchoring section 414, 416, there is provided an enlarged axially extending upper body portion 418, so that the upper body portion 418 is approximately equal in length to the lower body portion 28 of the anchoring sections. A chamfered or tapered portion 420 connects each enlarged upper body portion 418 to the smaller diameter, lower body portion 28. Preferably, the enlarged upper body portion 418 is provided with threads 422 or grooves 424 therein to provide retention means for the superstructure formed on the dentition. As shown in FIG. 13, the enlarged upper body portion 418 having a major diameter of approximately 0.028 inches, is larger than the minor diameter 72 and the thread 30 having a major diameter of approximately 0.024 inches as set forth above, of the anchoring section portion 414, 416. Thus, the enlarged body portion 418 defines a stop member for limiting the depth of insertion of the anchoring section portions 414, 416 into the channel formed in the tooth, as will be described below by way of example.

FIG. 14 illustrates the channels 56 being formed in the dentin or body 48, the channels 56 extending from the excavated surfaces 54 of the tooth 44. As shown, the conventional spiral drill 55 is urged into the dentin in a conventional manner, as set forth above, each channel having a seat portion 68 as mentioned above. It is noted again, that the dimension 66, representing the major diameter of the drilled channel 56, is less than the major diameter of the threaded dental anchoring sections of the above-mentioned dental anchors 110, 210, 310 and 410, so that these dental anchors can be self-threaded into the channel 56. Accordingly, the major diameter 66 of the channel 56 is also less than the major dimensions of the body portions or stop members 118, 218, 318, 418. It is further noted, that the depth of each channel 56 is greater than the distance from the pilot or distal end 36 of each dental anchor to the body portions or stop members 118, 218, 318, 418, for the reason set forth below. The insertion of the dental anchors 110, 210, 310 and 410 into the channels 56 of the tooth 44 will now be described, where by way of example, only the insertion of the dental anchor 110 will be explained, whereby the insertion of the other modified dental anchors 210, 310, and 410 is the same and therefore, an explanation thereof is not thought necessary.

FIG. 14 is similar to FIGS. 3 and 4, showing two modified dental anchors 110 of the present invention inserted into the channels 56 provided in the tooth 44, and a third dental anchor 110 being inserted into a third channel 56. Because the stop member 118 of the dental anchor 110 engages the perimeter of the mouth of the channel 56 as the dental anchor 110 is being self-threaded therein, the engagement thereof resists further rotation and will activate the self-shearing mechanism thereof so that the reduced thickness portion 38, or 26, of the dental anchor 110 will shear, thus terminating the insertion operation of the dental anchor 110. Accordingly, the pilot or distal end 36 of the dental anchor 110 does not reach the seat portion 68 of the channels 56, wherein the depth length of each channel 56 is longer than the distance between the pilot or distal end 36 and the stop member 118 of the distal anchor 110.

Therefore, even though the self-threading of the dental anchor 110 is faster and easier to install than the prior art dental anchor 58, the stresses at the seat portion 68 of the channels 56 are substantially reduced, or eliminated, due to the fact that the pilot or distal end 36 of the dental anchor 110 does not reach or engage the seat portion 68 because of the stop member 118 of the dental anchor 110. Furthermore, the shearing of the dental anchor 110 is more predictable because each dental anchor 110 will shear when the stop member 118 engages the mouth of the channel 56, thereby providing a consistent insertion of the dental anchor 110. Additionally, when the upper exposed portions of the dental anchor 110 are bent or cut after insertion thereof, and before the superstructure is formed on the tooth 44, there obviously will be minimal or no stresses produced at the seat 68 of the channels 56.

Referring now to FIGS. 16 and 19, there is illustrated a dental anchor 510 in accordance with another embodiment of the present invention. The dental anchor 510 includes a manipulating end section 512, an intermediate threaded anchoring section 514, and a lower threaded anchoring section 516. Manipulating end section 512 is similarly constructed as in the first embodiment shown in FIG. 1. Each of the threaded anchoring sections 514, 516 include an unthreaded body portion 118 of the type shown in FIG. 6, which has a larger diameter than the minor diameter of the threaded sections and defines a stop member for limiting the depth of insertion of the anchoring sections 514, 516, as previously described.

Each of the anchoring sections 514, 516 has an upper chamfered end 34 and an oppositely tapered pilot or distal end 36. The chamfered end 34 has a 45 degree bevel thereon, while the chamfered end 36 has a taper of approximately 20 degrees. Reduced thickness portion 26 is disposed between the manipulating end section 512 and the threaded anchoring section 516 to define a frangible section therebetween. Similarly, a reduced thickness portion 38 is defined between the lower and the intermediate threaded anchoring sections 516 and 514 to define a second frangible portion therebetween.

The anchoring sections 514 and 516 are similar, and therefore only one of these sections will be more fully described. Each of the anchoring sections 514, 516 has a body portion 518 provided with a helical thread 520. The thread is a buttress type thread having a substantially planar upper surface 522 with an angled or beveled lower surface 524 and a flattened crest portion 526 therebetween. The threads per inch are in the range of 60–100, as set forth above, wherein 96 threads per inch are preferred in the embodiments of FIGS. 16–20, which provides a pitch of approximately 0.010 inches. Therefore, each anchoring section 514, 516 would preferably have approximately 8 to 9 threads per each part of the section above and below the enlarged collar portion 118 to provide a total number of threads per section of between 16 and 18. It should be appreciated that the drawings show the general range between 60–100 threads per inch.

The angle of the beveled lower surface 524 of each thread is approximately 45 degrees. The minor diameter of the pin portion is approximately 0.020 inches with the major diameter of the entire pin being approximately 0.024 inches. Accordingly, the depth of each thread is approximately 0.020 inches. The threads are spaced apart from each other so that a portion of the minor diameter exists between the roots of adjacent threads. Thus, the threads are not a continuous saw tooth arrangement, but are spaced apart. The height of the distal end 36 from the lowermost thread is about 0.008 inches. The height of the collar portion 118 is approximately 0.010 inches.

FIG. 20 shows an enlarged section of the body 48 of the tooth, as was shown in FIG. 5, where the section is extended in order to provide a comparison between the dimensions of the first embodiment of the dental anchor shown generally at 10, and the second embodiment of the dental anchor shown generally at 510.

The dental anchor 10 of the first embodiment has a minor diameter of 0.019 inches, with a major diameter of 0.024 inches. The standard size of the hole is 0.021 inches. Accordingly, the clearance between the minor diameter and the drilled channel 56 is 0.0010 inches. In the anchor 10, a standard thread construction is utilized to provide upper and lower beveled edges, with a preferred thread of 84 threads per inch according to the invention. In the dental anchor 510, a buttress type thread is used with a preferred 96 threads per inch. With dental anchor 510, there is provided reduced stress in the tooth material since there is less displacement of dentin between the adjacent threads. The minor diameter can therefore be increased slightly to 0.020 inches. Utilizing the same channel 56 having a diameter of 0.021 inches, there results a clearance space on either side between the minor diameter and the channel of 0.005 inches. The smaller the clearance space between the minor diameter and the channel, the greater the retention capabilities of the dental pin.

It should be appreciated, that although the pin 510 of the second embodiment can produce less stress than the pin 10 of the first embodiment, a slightly greater number of rotations are required to seat the pin 510 of the second embodiment. Nevertheless, both embodiments require substantially less number of rotations than in the prior art. Typical prior art pins had approximately 124 threads per inch requiring at least 10 to 12 rotations for seating the pin. The embodiment shown in FIG. 16 requires only 8 rotations for seating.

The manipulating ends of the dental pins of the present invention can have any suitable structure for utilization with manual or automatic handpieces. As shown in FIG. 7, a manipulating end 612 of a dental anchor 610 is shown having a conventional tang 614 of oval shape extending from a cylindrical body portion 616. The tang 614 can be received in a conventional hand driver or wrench. The reduced section 26 is provided to separate the manipulating end 612 from a lower anchoring section 618.

As shown in FIG. 18, the manipulating end 714 of a dental anchor 710 can have a tang 716 formed as an integral part of the anchoring portion 718 without a frangible section therebetween. The tang 714 is connected directly to the pin body 720 on which the anchoring section 718 is formed. Various types of manipulating ends can be utilized on the anchors of the present invention, in accordance with those heretofore described in the aforementioned patents as well as those known in the prior art.

In the various embodiments shown, there were provided a tapered lead at the forward end for easy pin placement and for appropriate seating in spaced relationship from the bottom of the channel. The utilization of a shoulder stop at various sections provided for consistent full-depth pin insertion and guaranteed automatic pin shearing. The shear points were well defined for clear visual reference in order to see precisely where the pins shear. Additionally, by utilization of the buttress thread, there is provided increased retention, rapid insertion and minimal dentin displacement.

It is noted, the dental anchors 10, 110, 210, 310, 410, 510, 610 and 710 of the present invention, like the prior art dental anchor 58, can be fabricated from any suitable material known in the dental art, such material including precious metals or non-precious metals, or even suitable plastic material.

Numberous alterations of the structure herein disclosed will suggest themselves to those skilled in the art. However, it is to be understood, that the present disclosure relates to preferred embodiments of the invention which are for the purpose of illustration only, and are not to be construed as limitations of the invention.

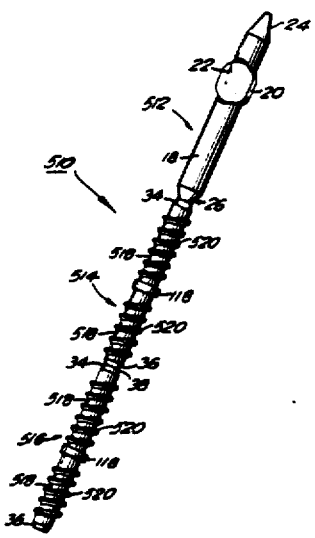

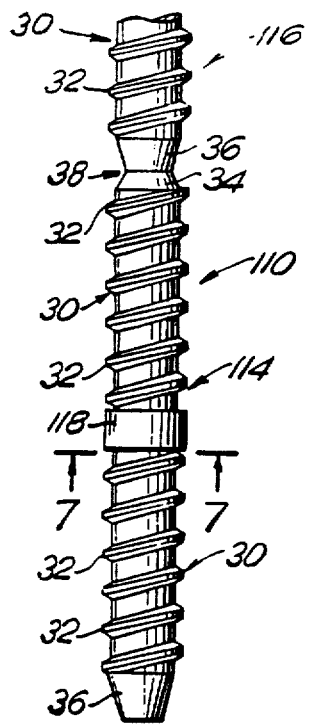
FIG.6
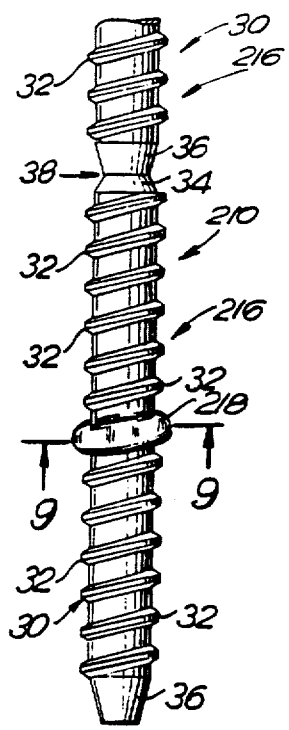
FIG.8
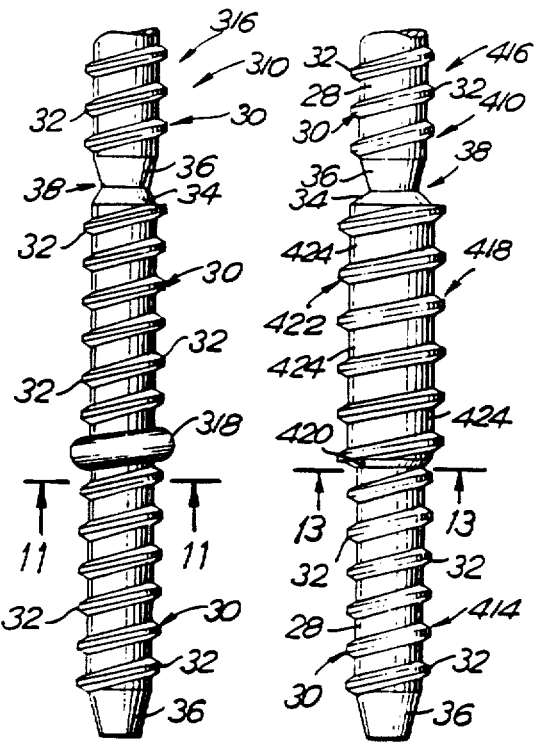
FIG.10   FIG.12
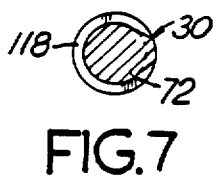
FIG.7
FIG.9
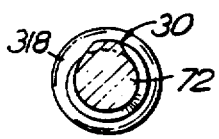
FIG.11
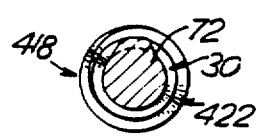
FIG.13
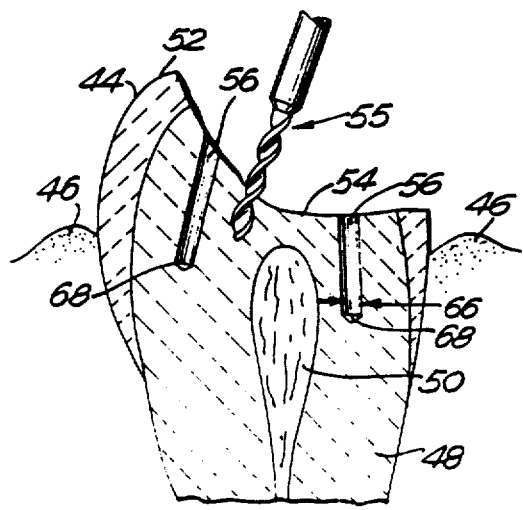
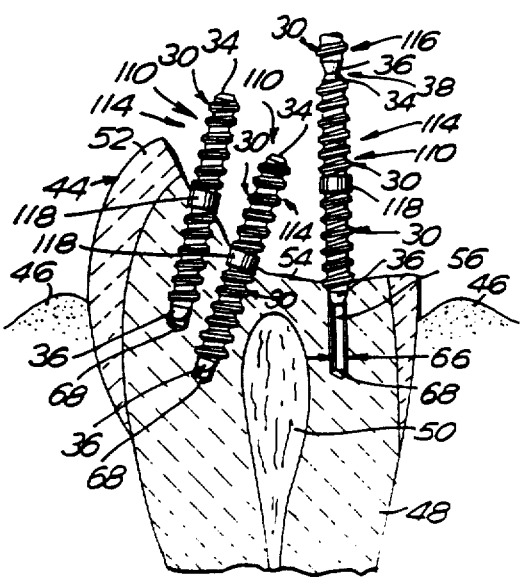

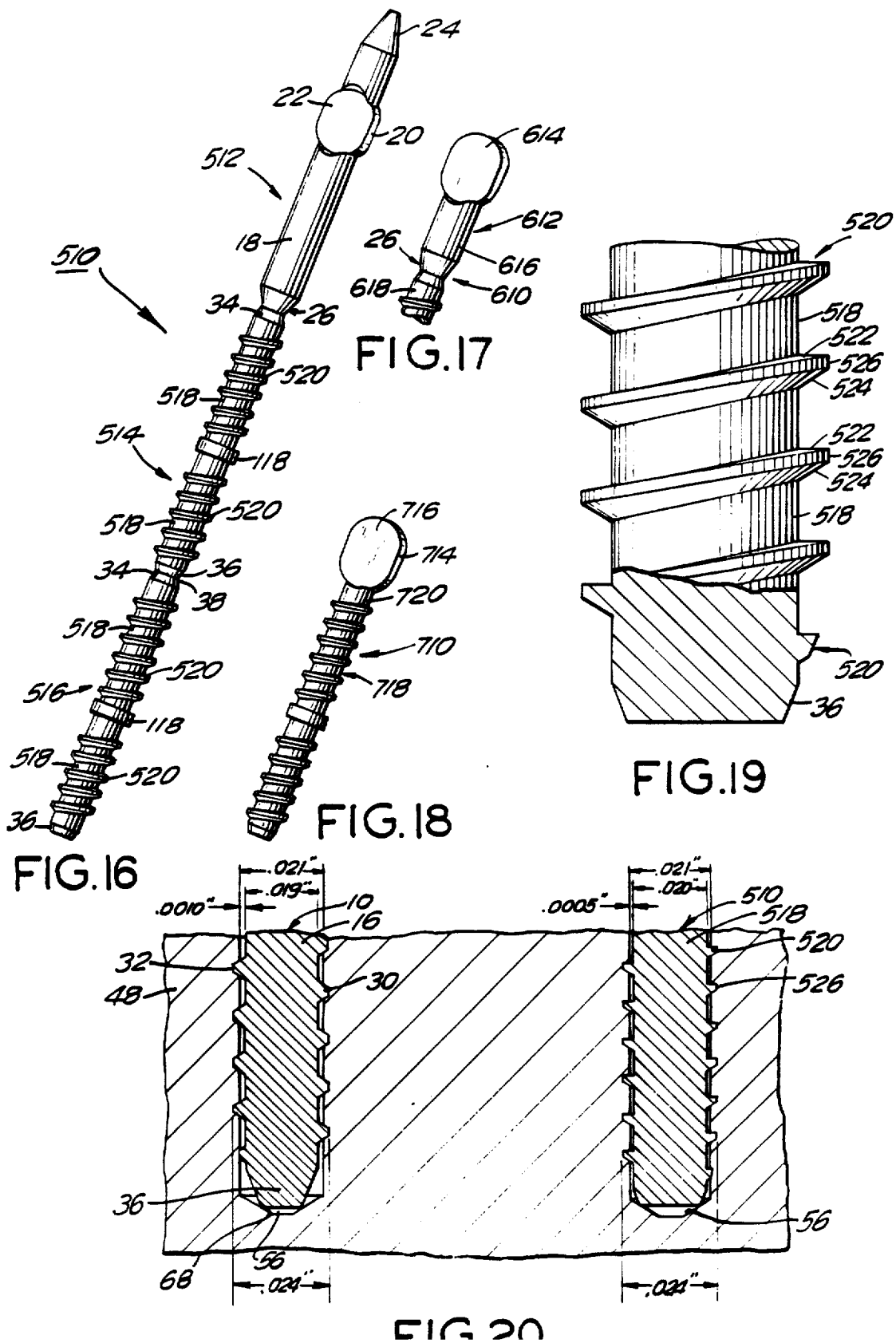

What is claimed is:

1. A dental anchor for insertion in a blind channel extending from an excavated surface of a tooth, the channel being confined within the tooth and having a major diameter of approximately 0.021 inches and a tapered seat portion of approximately 118 degrees, said dental anchor comprising at least one anchoring section having a manipulating end section at a proximal end thereof for permitting coupling thereof to a cooperating driving tool, said anchoring section having a major diameter of approximately 0.024 inches, said anchoring section including a plurality of self-threading buttress type threads having approximately a 0.010 inch pitch with adjacent crests of said threads being spaced apart by a distance greater than height of the threads, said anchoring section having a minor diameter of approximately 0.020 inches to provide a threaded height of approximately 0.0020 inches, said anchoring section having approximately 16 to 18 threads thereon, said anchoring section having a distal pilot end portion elongated in the axial direction, means for reducing stress at the seat portion of the channel by providing a minimum of contact between said anchoring section and the seat portion, said means including providing said pilot end portion with an elongated length approximately equal to said thread pitch to substantially space said threads from the seat portion and with an approximately 20 degree taper thereon downwardly from said anchoring section to reduce contact with channel walls, whereby said thread pitch provides for fast insertion of said dental anchor with minimal torque, and provides for a retention with reduced stresses, and said anchoring section including stop means disposed approximately midway along its length for limiting the depth of insertion thereof into the channel extending from the excavated surface of the tooth, so that the distal pilot end portion is prevented from engaging in the seat portion of the channel.

2. A dental anchor as in claim 1, wherein said dental anchor includes a second threaded anchoring section connected to said distal pilot end portion of said first mentioned anchoring section to provide a frangible reduced thickness portion therebetween which is readily visible.

3. A dental anchor for insertion into a channel extending from an excavated surface of a tooth, said dental anchor comprising at least one anchoring section having a manipulating end section at a proximal end thereof for permitting coupling thereof to a cooperating driving tool, said anchoring section including a plurality of self-threading threads defined by axially spaced apart crests, said threaded anchoring section having a major diameter larger than the diameter of the channel and being in the range of 60 to 100 threads per inch, said threads per inch providing for fast insertion of said dental anchor with minimum torque, and said self-threading threads being buttress type threads, said anchoring section including stop means disposed along its length for limiting the depth of insertion thereof into the channel so that a distal pilot end portion of said anchoring section is prevented from engaging in a seat portion of the channel, said pilot end portion being unthreaded and tapered downwardly from said anchoring section to facilitate insertion of said dental anchor into the channel and to reduce stresses adjacent to the seat portion of the channel after said dental anchor has been fully inserted into the channel, said stop means being disposed approximately midway along the length of said anchoring section with the midway length of said anchoring section being less than the channel length to space said pilot end portion from the seat portion of the channel when said stop means engages the excavated surface of the tooth.

4. A dental anchor as in claim 3, wherein said anchoring section has 96 threads per inch, and said major diameter is approximately 0.024 inches.

5. A dental anchor as in claim 3, wherein said threads have a 0.010 inch pitch.

6. A dental anchor as in claim 3, wherein said distal pilot end portion is elongated in the axial direction, said pilot end portion being approximately equal to the distance between the threads.

7. A dental anchor as in claim 6, wherein said dental anchor includes a second thread anchoring section connected to said distal pilot end portion of said first mentioned anchoring section to provide a frangible reduced thickness portion therebetween which is readily visible.

8. A dental anchor as in claim 3, wherein each thread has a height of between 0.0020 and 0.0025 inches.

9. A dental anchor as in claim 3, wherein said stop means includes an unthreaded portion having a diameter equal to said major diameter.

10. A dental anchor as in claim 3, wherein said stop means includes an extended portion having a transverse dimension larger than said major diameter.

11. A dental anchor as in claim 3, wherein said stop means includes a cylindrical portion having a transverse dimension larger than said major diameter.

12. A dental anchor as in claim 3, wherein said stop means includes a cylindrical portion extending from approximately a midway point to an opposite end of said anchoring section spaced from said distal pilot end portion, said cylindrical portion having a larger diameter than said major diameter.

13. A dental anchor as in claim 12, wherein said cylindrical portion includes retention means to retain a superstructure on the tooth, said retention means including threads.

14. A dental anchor as in claim 12, wherein said cylindrical portion includes retention means to retain a superstructure on the tooth, said retention means including grooves.

* * * * *

UNITED STATES PATENT AND TRADEMARK OFFICE
CERTIFICATE OF CORRECTION

PATENT NO. : 4,767,332
DATED : August 30, 1988
INVENTOR(S) : Bernard Weisman

It is certified that error appears in the above-identified patent and that said Letters Patent is hereby corrected as shown below:

The title page should appear as shown on the attached sheet.

The drawings consisting of figures 1-20 should appear as shown on the attached sheets.

To Apply To The Grant Only.

Signed and Sealed this

Thirteenth Day of February, 1990

*Attest:*

JEFFREY M. SAMUELS

*Attesting Officer*  *Acting Commissioner of Patents and Trademarks*

United States Patent [19]

Weissman

[11] Patent Number: 4,767,332

[45] Date of Patent: Aug. 30, 1988

[54] THREADED DENTAL ANCHOR

[75] Inventor: Bernard Weissman, New York, N.Y.

[73] Assignee: IPCO Corporation, White Plains, N.Y.

[21] Appl. No.: 517,006

[22] Filed: Jul. 25, 1983

Related U.S. Application Data

[63] Continuation-in-part of Ser. No. 361,522, Mar. 23, 1982, abandoned, and a continuation-in-part of Ser. No. 326,851, Dec. 3, 1981.

[51] Int. Cl.⁴ .................................................. A61C 5/04
[52] U.S. Cl. ............................................................ 433/225
[58] Field of Search .................... 433/225, 220, 174; 44/387, 420, 421

[56] References Cited

U.S. PATENT DOCUMENTS

| | | | |
|---|---|---|---|
| 4,103,422 | 8/1978 | Weiss et al. | 433/174 |
| 4,171,569 | 10/1979 | Rouins | 433/225 |
| 4,365,958 | 12/1982 | Vlock | 433/225 |

FOREIGN PATENT DOCUMENTS 2255916  5/1974  Fed. Rep. of Germany ...... 433/174

*Primary Examiner*—Robert Peshock
*Attorney, Agent, or Firm*—Goodman & Teitelbaum

[57] ABSTRACT

A self-threading dental anchor including a proximal head end providing a manipulating end section for permitting the coupling thereof to a cooperating driving tool, and a threaded anchoring portion extending from the proximal head end. The anchoring portion threads are in the range of 60–100 threads per inch, preferably 84 threads per inch with standard threads and 96 threads per inch with a buttress type thread, to provide for fast insertion with minimum torque. The anchoring portion has an elongated distal pilot end portion in the axial direction approximately equal to the thread pitch of approximately 0.010 to 0.012 inches. A second threaded anchoring portion may be connected to the distal pilot end portion of the first mentioned anchoring portion to provide a frangible reduced thickness portion therebetween, which is readily visible. Preferably, each thread has a height of approximately 0.0020 to 0.0025 inches. Modified embodiments of the dental anchor are provided with stop members spaced preferably midway along the length of each anchoring portion to limit the depth of insertion thereof into a channel which extends into a tooth understructure. The stop members can be formed by providing an unthreaded portion, by deforming, heading, offsetting, stamping, splaying, and the like.

14 Claims, 4 Drawing Sheets